United States Patent [19]

Jommi et al.

[11] Patent Number: 5,243,056

[45] Date of Patent: Sep. 7, 1993

[54] INTERMEDIATES FOR THE PREPARATION OF 1-(PHENYL)-1-HYDROXY-2-AMINO-3-FLUORO PROPANE DERIVATIVES

[75] Inventors: Giancarlo Jommi, Milan; Dario Chiarino, Monza, both of Italy

[73] Assignee: Zambon S.p.A., Vicenza, Italy

[21] Appl. No.: 841,075

[22] Filed: Feb. 25, 1992

Related U.S. Application Data

[60] Division of Ser. No. 162,247, Feb. 29, 1988, Pat. No. 5,105,009, which is a continuation of Ser. No. 616,086, Jun. 1, 1984, abandoned.

[30] Foreign Application Priority Data

Jun. 2, 1983 [IT]  Italy ............... 21417 A/83
Aug. 5, 1983 [IT]  Italy ............... 22449 A/83

[51] Int. Cl.$^5$ ............................ C07O 263/10
[52] U.S. Cl. .................... 548/232; 548/110; 548/237
[58] Field of Search ............ 548/232, 216, 215, 110

[56] References Cited

U.S. PATENT DOCUMENTS

| | | | |
|---|---|---|---|
| 2,717,268 | 9/1955 | Rebstock et al. | 561/144 |
| 2,727,042 | 12/1955 | Jacob | 564/212 X |
| 2,820,041 | 1/1958 | Heywood | . |
| 2,824,878 | 2/1958 | Alberti et al. | 548/232 |
| 4,179,442 | 12/1979 | Köllensperger et al. | 548/232 |
| 4,186,129 | 1/1980 | Huth | 548/232 |
| 4,188,402 | 2/1980 | Portelli et al. | 564/212 X |
| 4,235,892 | 11/1980 | Nagabhushan | 514/522 |
| 4,743,700 | 5/1988 | Jommi et al. | 548/229 |
| 4,876,352 | 10/1989 | Schumacher et al. | 548/229 |
| 4,918,095 | 4/1990 | DellaBella et al. | 548/238 |
| 5,105,009 | 4/1992 | Jommi et al. | 548/232 |

FOREIGN PATENT DOCUMENTS

| | | |
|---|---|---|
| 179022 | 7/1954 | Austria . |
| 876750 | 7/1971 | Canada ............... 564/359 |
| 0014437 | 8/1980 | European Pat. Off. . |
| 0130633 | 1/1985 | European Pat. Off. ....... 548/232 |
| 423705 | 4/1991 | European Pat. Off. . |
| 1058523 | 9/1952 | Fed. Rep. of Germany ...... 548/215 |

OTHER PUBLICATIONS

Merck Index, 10th Ed., Merck & Co., Rahway, N.J. 1983, pp. 289 and 1332.
Giordano et al. Jour. Org. Chem. vol. 56 pp. 6114–6118 (Oct. 1991).
Villa et al. Chem. Abstr. vol. 115, entry 71094n abstracting EP 423705.
Greene and Wuts, "Protective Groups in Organic Synthesis", 2nd Ed., pp. 31–34, 36–38, and 68–86.
Jommi et al., *Gazetta Chimica Italiana*, vol. 118, pp. 75–76, (1988).
Jommi et al., *Gazzetta Chimica Italiana*, vol. 116, pp. 485–489 (1986).

*Primary Examiner*—Donald G. Daus
*Attorney, Agent, or Firm*—Oblon, Spivak, McClelland, Maier & Neustadt

[57] ABSTRACT

Intermediates of Formula $$R-\text{C}_6\text{H}_4-\underset{\underset{\underset{X_1}{\overset{|}{C}}}{\overset{|}{O}}}{\text{CH}}-\underset{\underset{X_2}{}}{\overset{\underset{|}{N-X_3}}{\text{CH}}}-\text{CH}_2X_4 \quad (I)$$

where
R is a methylthio, methylsulfoxy, methylsulfonyl or a nitro group; and
X1 is hydrogen, 1-6 C alkyl, 1-6 C haloalkyl, 3-6 C cycloalkyl, phenyl or phenylalkyl(1-6 C), where the phenyl ring may be substituted by one or two halogen, 1-3 C alkyl, 1-3 C alkoxy or nitro; or
X1 together with X2 is an oxygen atom or an alkylene having from two to five Carbon atoms; or
X1 together with X2 and R4 is a chain of formula
(Abstract continued on next page.)

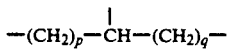

where p is 3 or 4 and q is 1 or 2; and

X2 is hydrogen, 1-6 C alkyl, 1-6 C haloalkyl, 3-6 C cycloalkyl or phenyl which may be substituted by one or two halogen, 1-3 C alkyl, 1-3 C alkoxy or nitro; or X2 together with X1 has the above mentioned meanings; or X2 together with R4 is —(CH$_2$)$_m$—CH=CH—; —(CH$_2$)$_m$—CH$_2$—CH$_2$—

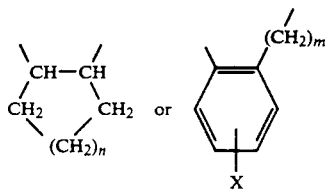

where n is 1 or 2; m is 0 or 1; X is hydrogen, halogen, 1-3 C alkyl, 1-3 C alkoxy or nitro; or X2 together with X1 and R4 has the above mentioned meanings; and X3 is hydrogen or —CO—R4 where R4 is hydrogen, 1-6 alkyl, 1-6 C haloalkyl, 3-6 C cycloalkyl, phenylalkyl(1-6 C) or phenyl where the phenyl ring may be substituted by one or two halogen, 1-3 C alkyl, 1-3 C alkoxy or nitro; or R4 together with X2 has the above mentioned meanings; or R4 together with X2 and X1 has the above mentioned meanings; and X4 is —OH, fluorine, OCOAlkyl(1-4 C), —O—trialkyl(1-6 C)silyl, —O—tetrahydropyranyl, —O—tetrahydrofuranyl or —O—SO$_2$R6 where R6 is methyl, trifluoromethyl, phenyl or p-methylphenylprovided, however, that X4 is not OH when R is a nitro group;

for the preparation of 1-(phenyl)-1-hydroxy-2-amino-3-fluoropropane derivatives.

7 Claims, No Drawings

INTERMEDIATES FOR THE PREPARATION OF 1-(PHENYL)-1-HYDROXY-2-AMINO-3-FLUORO PROPANE DERIVATIVES

This is a division of application Ser. No. 07/162,247 U.S. Pat. No. 5,105,009, filed Feb. 29, 1988, which is a continuation of Ser. No. 06/616,086 now abandoned, filed Jun. 1, 1984.

This invention relates to new intermediates useful for preparing 1-(phenyl)-1-hydroxy-2-amino-3-fluoro-propane derivatives.

More particularly this invention relates to new Compounds of Formula

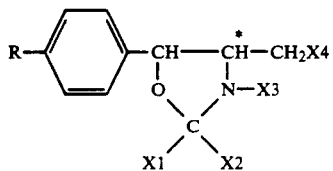

where
R is a methylthio, methylsulfoxy, methylsulfonyl or a nitro group; and
X1 is hydrogen, 1-6 C alkyl, 1-6 C haloalkyl, 3-6 C cycloalkyl, phenyl or phenylalkyl(1-6 C), where the phenyl ring may be substituted by one or two halogen, 1-3 C alkyl, 1-3 C alkoxy or nitro; or
X1 together with X2 is an oxygen atom or an alkylene having from two to five Carbon atoms; or
X1 together with X2 and R4 is a chain of formula

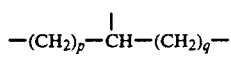

where p is 3 or 4 and q is 1 or 2; and
X2 is hydrogen, 1-6 C alkyl, 1-6 C haloalkyl, 3-6 C cycloalkyl or phenyl which may be substituted by one or two halogen, 1-3 C alkyl, 1-3 C alkoxy or nitro; or
X2 together with X1 has the above mentioned meanings;
X2 together with R4 is

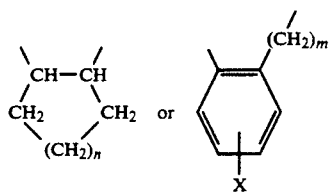

where
n is 1 or 2; m is 0 or 1; X is hydrogen, halogen, 1-3 C alkyl, 1-3 C alkoxy or nitro; or
X2 together with X1 and R4 has the above mentioned meanings; and
X3 is hydrogen or —CO—R4 where R4 is hydrogen, 1-6 alkyl, 1-6 C haloalkyl, 3-6 C cycloalkyl, phenylalkyl(1-6 C) or phenyl where the phenyl ring may be substituted by one or two halogen, 1-3 C alkyl, 1-3 C alkoxy or nitro; or
R4 together with X2 has the above mentioned meanings; or
R4 together with X2 and X1 has the above mentioned meanings; and
X4 is —OH, fluorine, OCOAlkyl(1-4 C), —O—trialkyl(1-6 C)silyl, —O—tetrahydropyranyl, —O—tetrahydrofuranyl or —O—SO₂R6 where R6 is methyl, trifluoromethyl, phenyl or p-methylphenyl provided, however, that X4 is not OH when R is a nitro group.

which are useful as intermediates for preparing Compounds of Formula:

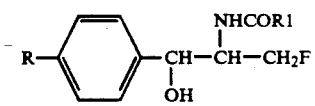

wherein
R is —NO₂, CH₃S—, CH₃SO—, and CH₃SO₂; and
R1 is mono-, di-, and tri-halomethyl.

The Compounds of Formula II contain two asymetric carbon atoms and can exist as steroisomers. Unless otherwise specified herein or in the claims, it is intended that all four stereoisomers are included, whether separated or mixtures thereof. The D-(threo)-forms are preferred because of their broader antibacterial activity.

U.S. Pat. No. 4,235,892 discloses the Compounds of Formula II and a process for their preparation. This process essentially consists of N-protecting a 1-(phenyl)-2-amino-1,3-propanediol, (the phenyl moiety of which is variously substituted) by an imido derivative of a dicarboxylic acid, of treating the thus obtained compound with dialkylaminosulfotrifluoride (DAST), of removing the N-protecting group and then in acylating the thus obtained 1-(phenyl)-1-hydroxy-2-amino-3-fluoro-propane with the desired haloacetic acid or with a suitable reactive derivative thereof.

Although apparently easy, this process suffers many disadvantages and affords low yields.

One of the main disadvantages is that the fluorination of the primary hydroxy group is not selective and leads to the formation of many byproducts, among which may be mentioned, for instance, the products deriving from the substitution at the secondary hydroxy group. The desired compound may thus be obtained at a sufficient degree of purity only by a particularly complex column chromatography process. Another disadvantage is that DAST is the only agent which allows performance of the fluorination step on the peculiar intermediate products which are prepared according to the process of U.S. Pat. No. 4,235,892 and DAST is very expensive and dangerous, especially when it is intended for large scale production.

It has now been found that the above mentioned disadvantages can be overcome by using new Compounds of Formula I wherein either the amino group or the secondary hydroxy group of the 1-(phenyl)-2-amino 1,3-propanediol derivative are protected.

Preferably also the primary hydroxy group is substituted by a leaving group which can be replaced by a fluorine atom.

The Compounds of Formula I have the advantage of avoiding the formation of many by-products and this not only in that the protection hinders the fluorination of the secondary hydroxy group but also in that it insures the stability of the configuration of the asymmetric carbon atoms.

Furthermore the Compounds of Formula I are quite soluble in the most part of the aprotic organic solvents, thus allowing the fluorination step to be carried out also in homogeneous phase and under anhydrous and mild conditions.

Another advantage is that the Compounds of Formula I are prepared very easily by making use of cheap reactants and that the protective groups can be removed very easily as well after the completion of the fluorination step.

Still another advantage of the Compounds of Formula I is that the protection of the secondary hydroxy group allows the substitution of the primary hydroxy group with a suitable leaving group so that the fluorination step can be most conveniently carried out with fluorination agents which are cheaper and less dangerous than DAST.

The protection of the amino and of the secondary hydroxy group thus performed is substantially inert to those treatments that the molecule undergoes, more particularly with nucleophiles and bases, up to the fluorination step and can then be easily removed under mild conditions.

When X1, X2 and R4, independently represent hydrogen, 1-6 C alkyl, 1-6 C haloalkyl, 3-6 C cycloalkyl, phenyl or substituted phenyl, examples of suitable reactants are: aldehydes such as formaldehyde, acetaldehyde, α,α,β-trichlorobutyraldehyde, cyclohexanecarbaldehyde, valeraldehyde, caproaldehyde, benzaldehyde, p-methylbenzaldehyde, anisaldehyde, 4-chlorobenzaldehyde, 4-ethoxy-3-methoxy-benzaldehyde, 2,6-dinitrobenzaldehyde or ketones such as acetone diethylketone or hexylmethylketone for protecting the secondary hydroxy group and one hydrogen of the amino group, and acids such as acetic, dichloroacetic, trifluoroacetic, pivaloyl, benzoic, cyclohexanecarboxylic 2,4-dibromobenzoic, veratric, 2,5-dimethylbenzoic, phenylacetic or 4-nitrobenzoic acid, for protecting the second hydrogen of the amino group.

When X1 and X2, together, are an alkylene radical having from 2 to 5 carbon atoms, examples of suitable reactants are the cycloalkanones such as cyclopropanone, cyclopentanone or cyclohexanone.

When X1 together with X2 and R4 is a chain of formula

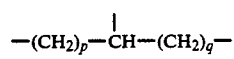

where p and q have the above mentioned meanings, examples of suitable reactants are the ketoacids such as (2-oxocyclopentyl) acetic acid, (2-oxocyclohexyl)-acetic acid, 3-(2-oxocyclopentyl) propionic acid and 3-(2-oxocyclohexyl)-propionic acid.

When X2 together with R4 forms a mono- or a polycyclic system, examples of suitable reactants are the aldehydo-acids or the keto-acids such as phthalaldehydic acid, succinic semialdehyde, levulinic acid, 4-phenyl-4-oxo-butyric acid; hexahydrophthalaldehydic acid; (2-acetyl)-cyclohexylcarboxylic acid and (2-acetyl)-cyclopentyl-carboxylic acid.

When X1 together with X2 is an oxygen atom, examples of suitable reactants are the halocarbonates of formula XCOOR2 where X is a halogen atom and R2 is an alkyl, aralkyl or an aryl radical; preferably R2 is an 1–4 C alkyl radical.

The methods for preparing the Compounds of Formula I change according to the nature of the desired Compound. Excepting those where X1 and X2 together are an oxygen atom, they can be prepared according to known techniques.

The preparation of Compounds I where X1 and X2, together, are an oxygen atom is based on the unexpected finding that compounds of Formula

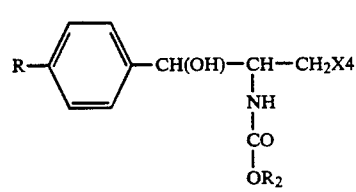

where R, X4 and R2 have the above mentioned meanings, cyclize regioselectively on the secondary hydroxy group to afford oxazolidinones of Formula I, in the presence of strong bases and of aprotic solvents.

The role of the solvent is critical. When the reaction is carried out in the presence of a non-aprotic solvent, the cyclization proceeds either on the secondary or on the primary hydroxy group and affords a mixture of the two possible cyclic compounds.

Examples of suitable aprotic solvents are the aromatic hydrocarbons such as benzene and toluene. Examples of suitable strong bases are the alkali and the alkaline earth metal alcoholates as well as the tertiary amines.

The cyclization reaction may also proceed via the intermediate formation of the alcoholate at the secondary hydroxy group when they are used alkali and alkaline earth metal alcoholates, alkali metal hydrides such as sodium hydride, sodium amide, Grignard-like organo-metallic derivatives and alkyl-lithium derivatives.

In their turn, the compounds (III) can be prepared according to known techniques such as the reaction of the desired 1-(phenyl)-2-amino-1,3-propanediol, substituted at the phenyl ring, with a compound of formula X-COOR2, where X is halogen and R2 has the above mentioned meanings, in the presence of a base and of a suitable diluent.

When it organic diluent is used such as acetonitrile, there is preferably used an organic base such as a tertiary amine whereas an inorganic base such as an alkali metal carbonate or bicarbonate is preferably used, when the reaction is carried out in aqueous medium. Alternatively a basic diluent such as pyridine may be used.

The compounds of formula III wherein R is —SCH3 are more soluble in the aprotic solvents, than those wherein R is —SO—CH3 or SO2CH3. A preferred way for preparing Compounds (I) wherein R is —SO—CH3 or —SO2—CH3 comprises the preparation of the corresponding Compounds (III) wherein R is —S—CH3, their subsequent cyclization and lastly, their oxidation according to known techniques.

The substitution of the hydrogen of the primary hydroxy group with a COAlkyl(1–4C) trialkyl(1–6C)-silyl, tetrahydropyranil, tetrahydrofuranyl and a —SO2R6 radical, where R6 has the above mentioned meanings, can be carried out before or after the protection of both the secondary hydroxy and amino group. Also this substitution can be carried out according to known techniques.

The fluorination of Compounds I where X4 is not fluorine can be carried out either with DAST or with less expensive and more amenable fluorination agents such as FAR (1-diethylamino-1,1-difluoro-2-chloro-2-fluoro-ethane), phosphorus fluoride, hydrofluoric acid optionally as a salt with soluble or polymeric tertiary amines and alkali and alkaline-earth metal fluorides.

Examples of suitable fluorination agents when X4 is —OH are FAR, phosphorus fluorides and hydrofluoric acid.

When FAR is used, the reaction is carried out under anhydrous conditions and in homogeneous phase, preferably in acetonitrile at the boiling temperature.

After performance of the fluorination step, the protective groups are removed from the Compounds of Formula I wherein X4 is fluorine.

A preferred method consists of removing the protective groups with acids, preferably inorganic acids, in aqueous medium or in water/organic diluents mixtures. The latter media are preferred when hydrolysis regenerates the compound or the compounds which had been previously used as protective agents and when the amine which is formed is soluble in an aqueous solution of inorganic acids. There is thus obtained a partition of the amine in the aqueous layer and of the protective agent or agents in the organic layer, from which they are recovered and then recycled; in its turn, the amine is recovered by precipitation via neutralization of the aqueous layer. Alternatively the amine can be extracted with a suitable organic solvent.

When X1 and X2, together are an oxygen atom, the protective group may also be removed through treatment with an organo-metallic derivative such as a Grignard's derivative and the subsequent hydrolysis in mild conditions with inorganic acids in water or in water/organic solvent mixtures.

Another possible method for removing the protective group when X1 and X2, together, are an oxygen atom, comprises the reduction of the keto group and the subsequent hydrolysis in mild conditions as described above. This reduction is preferably carried out with complex hydrides such as sodium borohydride.

After removal of the protective groups there is obtained a compound of Formula

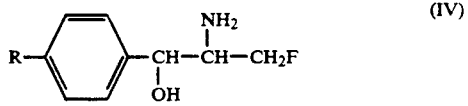

(IV)

which can be reacted with a haloacetic acid of Formula R1COOH, wherein R1 has the above mentioned meanings, or a reactive derivative thereof to afford the desired compound of Formula (II).

The protection performed by the Compounds of Formula I is useful not only for preparing the compounds of Formula II, but also whenever it is desired to replace the primary hydroxy group with another functional group, such as chlorine, bromine, iodine, nitrile, hydrogen, —OR7, —SR7, —SCOR7, —SCN, —S(=NH)NH2 —CH—(COOR7)2, wherein R7 is alkyl, aralkyl or aryl.

This invention is illustrated by the following examples which should not be constructed as limiting it in any way.

EXAMPLE 1

Preparation of 3-acetoxy-1-(4-methylsulfonyl-phenyl)-2-phthalimido-1-hydroxy-propane (A)

D-(threo)-1-(p-methylsulfonylphenyl)-2-phthalimido-1,3-propanediol (1 g; 2.66 mmols), prepared as described in U.S. Pat. No. 4,235,892, has been dissolved in anhydrous pyridine (5 ml). Acetylchloride (0.2 ml; 2.83 mmols) has been added dropwise to this solution kept under stirring at 0° C.; after completion of the addition, the reaction mixture has been heated to 25° C. and kept under stirring for 1 hour; afterwards, the reaction mixture has been poured into water and ice, acidified with hydrochloric acid and extracted with ethyl acetate.

The crude product (A) has been obtained (quantitative yield) from the organic layer after drying over sodium sulfate and evaporation of the solvent in vacuo; the crude, after crystallization from methanol, gave a pure product (0.84 g; yield 75%) as shown by HPLC and TLC analysis.

Elemental Analysis for $C_{20}H_{19}O_9N$: (found) C 57.3%; H 4.6%; N 3.3%; (Calculated) C 57.55%; H 4.56%; N 3.36%.

The acetylation is regio-selective on the secondary hydroxy group as shown by NMR spectrum in DMSO; delta=1.78; s, 3H, $CH_3CO$—; 4.50 dd- 2H, —$CH_2OAc$; 6.02,d,1H, benzylic OH.

EXAMPLE 2

Reduction of compound (A) to 3-acetoxy-1-(4-methylsulfonyl-phenyl)-1-hydroxy-2-(3-hydroxy-1H-isoindol-1-one-2-yl)-propane (B)

Compound (A) (0.76 g; 1.82 mmols) has been added to a mixture of tetrahydrofuran and water (1:1; 4 ml); to this suspension, kept at 0° C. under vigorous stirring, has been added portionwise sodium borohydride (138 mg; 3.64 mmols).

As the reaction proceeded, the suspension became a homogeneous solution, after 1 hour and after having checked by TLC the disappearance of compound (A) and the formation of a new product, tetrahydrofuran has been evaporated in vacuo and the product extracted with ethyl acetate.

After drying over sodium sulfate and evaporation of the solvent, compound (B) (0.7 g; yield 92%) has been obtained sufficiently pure to undergo as such the following reaction (Example 3).

Compound (B) proved to be a mixture of two diastereoisomers because of the formation, during the reduction step, of a new asymmetric carbon atom; this has been proved by TLC, HPLC and NMR spectra in DMSO containing $D_2O$; delta 1.78; s, and 1.86, s, 3H on the whole, $CH_3$—CO in two diastereoisomers in the ratio 35:65; 5.84, s, and 6.24,s,1H, on the whole

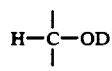

of the isoindole system (doublets, before deuteration, coupled with two doublets exhibiting delta=6.8 and 6.57 respectively, 1H on the whole for —OH in the two diastereoisomers) and, finally, 5.14, d, and 5.2, d, 1H on the whole for the two

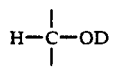

in position 1 of the propane chain.

EXAMPLE 3

Cyclization of compound (B) to 3-acetoxymethyl-2-(4-methylsulfonyl-phenyl)-2,3-dihydro-oxazole-[2,3,a]-isoindol-5(9bH)-one (C)

Product (B) (0.55 g; 1.3 mmol) has been suspended in benzene (5 ml) containing a little amount of p-toluensulfonic acid (5 mg); by heating, the mixture became a clear solution. A short time later the water formed during the reaction has been distilled azeotropically until water was absent in the distilled benzene and TLC analysis showed the disappearance of product (B). At the end, almost all benzene has been evaporated in vacuo; after having added some water, product (C) has been extracted with ethyl acetate. Crude product (C) has been obtained in quantitative yield from the organic phase after drying over sodium sulfate and evaporation of the solvent in vacuo.

Crude product (C) has been used as such for the subsequent hydrolysis (Example 4). An aliquot has been purified by chromatography on silica gel using ethyl acetate/petroleum ether in various ratios or pure ethyl acetate as eluants. It has been proved that the crude contained small amounts of some unidentified impurities; after purification by chromatography has been proved to be a mixture of two diastereoisomers as shown by TLC and HPLC analysis as well as by NMR spectrum in DMSO: delta 6.38,s, and 6.07 s, 1H on the whole,

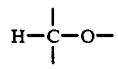

of the isoindole system; 2.08 s and 2.18 s, 3H on the whole, $CH_3CO$—; 3.19, s and 3.24, s, 3H on the whole, $CH_3SO_2$—.

Elemental analysis for $C_{20}H_{19}O_8N$: (calculated): C, 59.85%; H, 4.74%; N, 3.49; (found) C, 59.9%; H, 4.6%; N, 3.6%

EXAMPLE 4

Hydrolysis of compound (C) to 2-(4-methylsulfonyl-phenyl)-3-hydroxymethyl-2,3-dihydro-oxazole-[2,3,a]-isoindol-5(9bH)-one (D)

Product (C) (0.2 g; 0.5 mmols) has been dissolved in methanol (2 ml) containing potassium hydroxide (42 mg; 0.75 mmols) at 0° C. and under vigorous stirring. After 30' the hydrolysis has been checked by TLC and showed the disappearance of product (C).

Methanol has been evaporated in vacuo and in the cold; the residue has been treated with water and extracted with ethyl acetate. The organic layer has been dried and evaporated to afford product (D) which has been recrystallized from ethyl acetate (0.16 g; yield 89%). The presence of two diastereoisomers in product (D) has been shown by NMR spectrum in DMSO, delta = 6.3, s and 5.82,s, 1H on the whole,

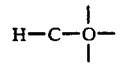

of the isoindole system; 3.18,s, and 3.22,s, 3H on the whole, $CH_3SO_2$—.

EXAMPLE 5

Preparation of 2-(4-methylsulfonyl-phenyl)-3-fluoromethyl-2,3-dihydroxazole-[2,3,a]-isoindol-(9bH)-one (E)

35 ml of anhydrous acetonitrile, cooled to 0° C., has been added with 3.2 ml (20 mmols) of FAR (1-diethylamino-1-difluoro-2-chloro-2-fluoroethane). After 10 minutes carefully dried compound (D) (5 g; 13.9 mmols) has been added portionwise; when the addition has been over, the solution has been refluxed for 2 hours. After completion of the reaction, the solvent has been evaporated in vacuo and the residue, after treatment with water and ice, has been extracted with ethyl acetate. The organic layer has been dried over sodium sulfate and evaporated in vacuo to afford crude (E), which has been used as such for the subsequent hydrolysis (Example 6); an aliquot has been purified by chromatography on silica gel and the diastereoisomer present in the mixture in largest amount has been isolated and showed a very high purity degree.

NMR spectrum in $CHCl_3$: delta = 3.04,s,3H, $CH_3SO_2$; 4.18,m,1H,

5.58, d, 1H, J = 6 cps, H—C—O—; 6.20, s, 1H,

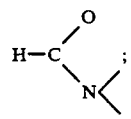

4.82, m, 2H, $J_{H_1F} = 48$ Hz.

EXAMPLE 6

Hydrolysis of compound (E) and preparation of D-threo-1-(4-methylsulfonyl-phenyl)-1-hydroxy-2-dichloroacetamido-3-fluoro-propane (F)

Compound (E) (2.07 g; 5.73 mmols) has been suspended in 2N HCl (60 ml) and the suspension refluxed for 7 hours.

After cooling, the mixture has been extracted with ethyl ether to recover the phthalaldehydic acid formed during the hydrolysis step.

The aqueous layer has been saturated with sodium chloride and potassium carbonate, extracted with ethyl acetate and then with chloroform.

The combined organic extracts has been dried over sodium sulfate and evaporated in vacuo. The crude product thus obtained, which, without further purification, has been treated, at the boiling temperature for 6 hours, with methyl dichloroacetate (6 ml) in the presence of catalytic amounts of triethylamine. After completion of the reaction, the volatile compounds has been removed and the residue has been chromatographed on silica gel while collecting the fractions containing (F). Compound (F) has been compared with a sample obtained according to another process (U.S. Pat. No. 4,235,892) and proved, by analytical and microbiological tests, to be identical with the sample.

EXAMPLE 7

Preparation of 2-(4-methylsulfonyl-phenyl)-3-methansulfonyloxymethyl-2,3-dihydro-oxazole[2,3,a]-isoindol-5-(9bH)-one (G)

Freshly distilled methanesulfonyl chloride (0.35 ml; 4.59 mmols) has been added to a solution of compound (D) (1.5 g; 4.17 mmols) in pyridine (3 ml), kept at 0° C. and under stirring. The mixture was allowed to stand in refrigerator overnight and then added with ice and extracted with ethyl acetate. The combined organic extracts has been dried over sodium sulfate and the solvent removed by evaporation.

Compound (G) has been thus obtained in a purity degree sufficient to undergo the subsequent reaction (Example 8).

EXAMPLE 8

Preparation of compound (E) from (G)

Compound (G) (1.48 g; 3.38 mmols) has been dissolved in warm toluene (7 ml). This solution was added with an aqueous solution of potassium fluoride (4 ml; solution consisting of 3 g of potassium fluoride and 3 g of water) and with hexadecyltributylphosphonium chloride (0.28 g).

The thus obtained heterogeneous mixture has been refluxed under vigorous stirring for 7 hours. The organic layer has been then separated and evaporated; the residue has been treated with water and extracted with ethyl acetate. The organic layer has been dried over sodium sulfate and evaporated to afford crude product (E) which has been purified by chromatography on silica gel. The thus obtained product showed the same characteristics as the product obtained according to Example 5.

EXAMPLE 9

Preparation of 1,3-dihydroxy-1-(4-methylthio-phenyl)-2-ethoxycarbonylamino-propane (H)

D-(threo)-1-(4-methylthio-phenyl)-2-amino-1,3-propanediol (1.06 g; 4.93 mmols) has been suspended into an aqueous solution of potassium carbonate (1.8 g of potassium carbonate into 20 ml of water) and the thus obtained mixture has been cooled, under vigorous stirring, to 0° C.

Ethyl chlorocarbonate (0.5 ml) has been dropped quickly into the mixture maintained under vigorous stirring at 0° C.; after half a hour, further 0.24 ml of ethyl chlorocarbonate (total amount: 7.74 mmols) has been added and the mixture has been maintained under stirring for 1 further hour.

At first the reaction mixture became clear and then a white precipitate has been slowly formed. After having checked the completion of the reaction by TLC, the suspension has been extracted with ethyl acetate. After drying on sodium sulfate, filtration and evaporation of the solvent, the organic extracts afforded 1.37 g of crude (H) (yield, 95.5%) which has been recrystallized from ethyl acetate/diisopropyl ether. m.p.=75° C.

I.R. spectrum: 3340 and 3450 cm$^{-1}$ (OH, NH stretching), 1690–1700 cm$^{-1}$ (broad band: C=O amide).

In a similar manner there has been prepared the 1,3-dihydroxy-1-(4-methylsulfonyl)-phenyl-2-ethoxycarbonylamino-propane (I) which, after crystallization from ethyl acetate, showed (IR analysis) the following peaks: 3200–3360 cm$^{-1}$ (broad band-OH and NH stretching), 1715 cm$^{-1}$ (CO amide).

EXAMPLE 10

Cyclization of compound (H) to 5-(4-methylthio-phenyl)-4-hydroxymethyl-oxazolidin-2-one (J)

Compound (H) (5 g; 17.5 mmols) has been dissolved in warm toluene (25 ml). To this solution, an equimolar amount of potassium tert. butylate has been added and the reaction mixture has been refluxed for 3 hours. Afterwards, almost all of the solvent has been evaporated; water and ice have been added to the residue and the precipitate has been collected by filtration. The thus obtained crude (J) has been recrystallized from ethanol (3.7 g; yield, 88%); m.p. 130°–131° C.

I.R. Spectrum: 3180, 3240, 3300 cm$^{-1}$ (OH an NH stretching) 1720; 1745 cm$^{-1}$ (C=O, oxazolidinone);

NMR in DMSO, delta: 7,64 and 8,0, two doublets, 2H each one of p-substituted phenyl; 7.88, S, 1H, NH amido; 5.48, d, 1H, benzyl hydrogen; 3.56, m, 2H, hydroxymethyl; 5.16, m, H linked to C4 of oxazolidinone ring; 3.2, S, 3H, CH$_3$S—.

EXAMPLE 11

Oxidation of compound (J) to 5-(4-methylsulfonyl-phenyl)-4-hydroxymethyl-oxazolidin-2-one (K)

Compound (J) (53 g; 221 mmols) has been added portionwise to 84 ml of hydrogen peroxide (130 vol.) maintained under stirring at 40°–45° C. After completion of the addition, the stirring has been continued for further 20 hours at 40° C.

Acetic anhydride (76.6 g; 20.7 ml) has been dropped into the reaction mixture by keeping the temperature below 40° C.

The reaction mixture has been then cooled to 20°–22° C. and maintained under stirring at this temperature for 3 hours and, finally, allowed to stand in refrigerator overnight.

Afterwards, the solvent has been evaporated with caution in vacuo at 40° C.; hot ethanol has been added to the thus obtained residue. The solvent has been again evaporated and the residue crystallized from methyl alcohol. 48.6 g of product (K) yield, 81%. m.p. 172°–174° C.

I.R. spectrum: 1710 cm$^{-1}$ (C=O, amide) 3470, 3340, 3250, 3200 cm$^{-1}$ (OH and NH).

EXAMPLE 12

Preparation of 5-(4-methylsulfonyl-phenyl)-4-fluoromethyl-oxazolidin-2-one (L) from (K)

To 1 ml of acetonitrile at 0° C. have been added two drops of FAR and, after some time, anhydrous compound (K) (100 mg; 0.42 mmols); afterwards, has been added the remaining aliquot of FAR (total amount: 1.5 mols to each mole of compound K); the suspension has been maintained under stirring at 0° C. for 10 minutes and the temperature has been then allowed to rise up to 20° C. When the suspension became clear it has been refluxed for 3 hours. After evaporation of the solvent, the residue has been treated with water and ethyl acetate. The organic extract has been dried over sodium sulfate, evaporated to dryness and the residue (90 mg) chromatographed on silica gel. Pure product (L) has been thus obtained (45 mg).

I.R. spectrum: 1750 cm$^{-1}$ (C=O, oxazolidinone)

N.M.R. in DMSO, delta: 7.70 and 8.05, two doublets, 2H each one of 4-substituted phenyl; 8.16, S, NH amido; 5.6, d, 1H, benzyl hydrogen; 4.74 and 4.5, two multiplets, 1H each.

EXAMPLE 13

Preparation of 5-(4-methylsulfonyl-phenyl)-4-methanesulfonyloxymethyl-oxazolidin-2-one (M) from (K)

Compound (K) (200 mg; 0.84 mmols) has been dissolved in anhydrous pyridine (3 ml). The thus obtained solution has been cooled to 0° C. and added with freshly distilled methanesulfonyl chloride (0.06 ml). The solution has been maintained at 0° C. overnight and then diluted with an aqueous solution of hydrochloric acid (stoichiometric amount with respect to pyridine) and ice. After extraction with ethyl acetate, the organic extract has been dried over sodium sulfate and evaporated in vacuo to afford crude (M); yield, 85–90%.

I.R. spectrum: 3300 cm$^{-1}$ (NH), 1760 and 1740 cm$^{-1}$.

EXAMPLE 14

Preparation of (L) from (M)

Product (M) (155 mg; 0.44 mmols) has been suspended into 0.5 ml of toluene; to this solution have been added hexadecyltributylphosphonium bromide (22.3 mg) and a concentrate solution of KF (207 mg; 2.2 mmols) in water.

The reaction mixture has been refluxed under vigorous stirring for 6 hours and then diluted with water. The aqueous layer has been extracted with ethyl acetate; the combined organic extracts have been dried over sodium sulfate, evaporated in vacuo and the crude residue (110 mg) has been chromatographed on silica gel to afford 40 mg of pure product (L).

We claim:

1. A compound of Formula

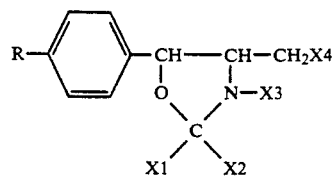

(I)

where
R is a methylthio, methylsulfoxy, methylsulfonyl or a nitro group;
X1 and X2 together are an oxygen atom;
X3 is hydrogen or —CO—R4 where R4 is hydrogen, C$_{1-6}$ alkyl, C$_{1-6}$ haloalkyl, C$_{3-6}$ cycloalkyl, phenyl or phenylalkyl(C$_{1-6}$) where the phenyl ring may be substituted by one or two halogen, C$_{1-3}$ alkyl, C$_{1-3}$ alkoxy or nitro; and
X4 is OCOAlkyl(C$_{1-4}$) or —O—SO$_2$R6 where R6 is methyl, trifluoromethyl, phenyl or p-methyl-phenyl.

2. The compound of claim 1, which is in the D-threo form.

3. The compound of claim 1, wherein X3 is H.

4. A compound of Formula

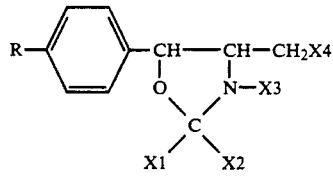

(I)

where
R is a methylthio, methylsulfoxy, methylsulfonyl or a nitro group;
X1 and X2 together are an oxygen atom;
X3 is hydrogen or —CO—R4 where R4 is hydrogen, C$_{1-6}$ alkyl, C$_{1-6}$ haloalkyl, C$_{3-6}$ cycloalkyl, phenyl or phenylalkyl(C$_{1-6}$) where the phenyl ring may be substituted by one or two halogen, C$_{1-3}$ alkyl, C$_{1-3}$ alkoxy or nitro; and X4 is fluorine.

5. The compound of claim 4, which is in the D-threo form.

6. The compound of claim 4, wherein X3 is H.

7. 5-(4-methylsulfonylphenyl)-4-fluoromethyl-oxazolidin-2-one.

* * * * *